United States Patent [19]

Orlowski et al.

[11] 4,422,967
[45] * Dec. 27, 1983

[54] PURIFICATION OF CALCITONIN BY PARTITION CHROMATOGRAPHY

[75] Inventors: Ronald C. Orlowski, Frankfort, Ill.; Charles M. Groginsky, Tucson, Ariz.; Jay K. Seyler, Bourbonnais, Ill.

[73] Assignee: Armour Pharmaceutical Company, Tuckahoe, N.Y.

[*] Notice: The portion of the term of this patent subsequent to Jun. 22, 1999, has been disclaimed.

[21] Appl. No.: 379,853

[22] Filed: May 19, 1982

Related U.S. Application Data

[63] Continuation-in-part of Ser. No. 189,812, Sep. 22, 1980, Pat. No. 4,336,187, which is a continuation-in-part of Ser. No. 94,323, Nov. 14, 1979, abandoned.

[51] Int. Cl.$^3$ ............................................ C07C 103/52
[52] U.S. Cl. ............................................. 260/112.5 T
[58] Field of Search ................................. 260/112.5 T

[56] References Cited

U.S. PATENT DOCUMENTS 4,336,187 6/1982 Orlowski et al. ............ 260/112.5 T

Primary Examiner—Delbert R. Phillips

[57] ABSTRACT

The purification of crude calcitonin by subjecting a crude calcitonin material to partition chromatography in which the solvent utilized is a mixture of butanol, a lower aliphatic alcohol, which is ethanol, methanol, or propanol, or mixtures thereof, acetic acid, water and ammonium acetate. In place of acetic acid and ammonium acetate, formic acid and ammonium formate may be used. The crude calcitonin of this invention is of a type known as ultimobronchial calcitonin. This includes calcitonins of the salmon and eel, whether the calcitonins of this type be obtained from natural sources or are prepared by synthesis. Preferably, the crude calcitonins of this type, which are purified by the process herein set forth, are obtained by solid phase synthesis in which the amino acid chain is assembled by attaching a resin support to the first amino acid, adding the amino acids one-by-one in the order in which they appear in the natural calcitonin, and finally removing the resin and the protective groups used in the synthesis.

12 Claims, No Drawings

PURIFICATION OF CALCITONIN BY PARTITION CHROMATOGRAPHY

This application is a continuation-in-part of our application Ser. No. 189,812, filed Sept. 22, 1980, now U.S. Pat. No. 4,336,187, which, in turn, is a continuation-in-part of Ser. No. 094,323, filed Nov. 14, 1979, now abandoned.

This invention relates to processes and procedures useful in purifying peptides having biological activities similar to that of the natural ultimobroncial calcitonin; and more particularly, to processes which utilize partition chromatography for separating the active calcitonin substance from other substance which do not have such activity and so may be regarded as impurities.

BACKGROUND

It has been known for some time that some of the hormone peptides can be derived from the glands of land and aquatic animals and that such hormones can be used to treat hormonal deficiencies in man and in animals. The adrenocorticotropic hormone is effective in treating deficiencies of this hormone, and calcitonin is effective in the treatment of Paget's Disease of the bone (see Seminars in Drug Treatment, Vol. 2, No. 1, 1972).

More recently, methods for the synthesis of substance containing hormonal activity have been discovered. For example, see Colescott et al, U.S. Pat. No. 3,915,949 disclosing the synthesis of adrencorticotropic hormone and U.S. Pat. No. 3,926,938 relating to the synthesis of calcitonin.

In order to utilize the crude materials which come from the synthesis of peptide hormones in the treatment of humans, it is necessary to purify the materials which come as a result of the synthesis. The classical methods heretofore used for this purification are tedious and time consuming, and usually result in low yields of the hormones. These classical methods are adaptable only to very small quantities of the materials. Examples of the methods heretofore used are found in Pat. No. 3,915,949 in Column 18 and Pat. No. 3,926,938 in Column 20.

We have sought new and improved methods for conducting the necessary purification of crude peptide hormone materials. We are aware that partition chromatography has been suggested for purifying certain hormone peptides (see *Journal of Chromatography*, pages 423–428; Elsevier Publishing Company, Amsterdam, Holland; CHROM. 5708).

In general, the procedure involved in carrying out partition chromatography is well known. This procedure includes packing a column, suitably using a fine dextran resin such as is sold under the trademark SEPHADEX. The resin may be prepared for use in the column by adding 4.5 kg. of the resin to 35 liters of 0.2 M acetic acid in a container and bringing the volume up to 40 liters to make an 8.5:1 ratio of solvent to resin. Some of the supernatant may be removed, resulting in about 5 liters of supernatant and 23 liters of suspended resin.

To prepare the column, the prepared resin may be poured into the column as a thick slurry. The volume of the resin at this stage (in liters) may be about five times its weight (in kilograms). The resin may be allowed to settle under a flow of 0.2 M acetic acid until it reaches a constant height.

The procedure of partition chromatography involves three essential steps in the following sequence:

(1) The equilibration of the column to lower phase,
(2) The equilibration of the column to upper phase, and
(3) The separation of the mixture into its components based on the individual differential partition coefficients of the components between the two phases of an immissible mixture of solvents.

The term "partition chromatography" when used herein, is taken to mean a purification procedure involving these three steps.

In an attempt to purify crude adrenocorticotropic hormone (ACTH) we obtained a quantity of this crude hormone prepared in accordance with the Colescott et al. U.S. Pat. No. 3,915,949 and subjected the crude hormone to a purification procedure by partition chromatography. This attempt and the results obtained are reported in the following paragraph:

A solution of 200 mg. of the crude ACTH prepared in accordance with the process of Pat. No. 3,915,949, in 20 ml. of upper phase from the system 1,200 ml. of n-butanol, 300 ml. of ethanol and 1,500 ml. of 0.2 M ammonium acetate containing 0.6 ml. of acetic acid, was placed on a dextran resin column, previously equilibrated with lower and then to upper phases of the solvent system, and was then eluted with upper phase. The effluent was collected in tubes on a fraction collector. A Folin-Lowry analysis showed that only very small traces of peptide had been eluted. This indicated to us that this partition system does not effectively move the ACTH down the column in the partition chromatography procedure. No improvement in the purity of the crude ACTH could be detected by thin layer chromatography.

We have also tried to purify crude human calcitonin using partition chromatography with substantially the same solvents and procedures as we have described in our attempts to purify ACTH. A description of these attempts is reported as follows:

A Folin-Lowry analysis of the collected fractions demonstrated that no separation of impurities from the desired hormone human calcitonin was achieved. The impurities and the human calcitonin co-eluted, and no separation was observed.

From the above, it is apparent that our attempts to purify crude human calcitonin using this partition chromatography solvent system did not produce a satisfactory purification process.

DESCRIPTION OF THE GENERAL TYPES OF CALCITONINS

Calcitonins are of two general types. One general type, which is obtained from the more primitive species including salmon or eel, is called ultimobronchial calcitonins. A second type, which is obtained from mammalian species in which the thyroid functions have been developed, is called thyrocalcitonins. Included in this second type of calcitonin are the calcitonins of the pig, cow, sheep, rat, human, and other species of mammalian animal origin.

Phyllogenetic studies have established that the ultimobranchia gland, found as a distinct organ in sub-mammalian species (from eel and salmon), is the evolutionary progenitor of the thyroid in mammals (man, pig, cow, rat, and sheep). See Parathyroid Hormone and Thyrocalcitonin proceedings of the Third Parathyroid Conference (R. V. Talmage, L. F. Belanger, and I. Clark, eds.), Excerpta Medica Foundation, New York, pages 43, 68–73.

The following Table I lists molecular structures for typical ultimobronchial calcitonins, and Table II lists molecular structures for some species of the thyrocalcitonins.

TABLE I

| Eel | Salmon I | Salmon II | Salmon III |
|---|---|---|---|
| Cys | | | |
| Ser | | | |
| Asn | | | |
| Leu | | | |
| Ser | | | |
| Thr | | | |
| Cys | | | |
| Val— — — — — — — — — — — | | | Met |
| Leu | | | |
| Gly | | | |
| Lys | | | |
| Leu | | | |
| Ser | | | |
| Gln | | | |
| Glu— — — — — — | | Asp | Asp |
| Leu | | | |
| His | | | |
| Lys | | | |
| Leu | | | |
| Gln | | | |
| Thr | | | |
| Tyr— — — — — — | | Phe | Phe |
| Pro | | | |
| Arg | | | |
| Thr | | | |
| Asp | Asn | Asn | Asn |
| Val | Thr | Thr | Thr |
| Gly | | | |
| Ala | Ser | | |
| Gly | | | |
| Thr— — — — — — | | Val | Val |
| Pro | | | |
| NH₂ | | | |

TABLE II

| Human | Bovine | Porcine | Ovine |
|---|---|---|---|
| Cys | | | |
| Gly— — — — | Ser— — — — | Ser— — — — | Ser |
| Asn | | | |
| Leu | | | |
| Ser | | | |
| Thr | | | |
| Cys | | | |
| Met— — — — | Val— — — — | Val— — — — | Val |
| Leu | | | |
| Gly | Ser | Ser | Ser |
| Thr | Ala | Ala | Ala |
| Tyr | Tyr | Tyr | Tyr |
| Thr | Trp | Trp | Trp |
| Gln | Lys | Arg | Lys |
| Asp | Asp | Asn | Asp |
| Phe— — — — | Leu— — — — | Leu— — — — | Leu |
| Asn | Asn | Asn | Asn |
| Lys | Asn | Asn | Asn |
| Phe | Tyr | Phe | Tyr |
| His | His | His | His |
| Thr | Arg | Arg | Arg |
| Phe | Phe | Phe | Tyr |
| Pro | Ser | Ser | Ser |
| Gln | Gly | Gly | Gly |
| Thr | Met | Met | Met |
| Ala | Gly | Gly | Gly |
| Ile | Phe | Phe | Phe |
| Gly | | | |
| Val | Pro | Pro | Pro |
| Gly | Glu | Glu | Glu |
| Ala | Thr | Thr | Thr |
| Pro | | | |
| NH₂ | | | |

Close examination of the amino acid sequences given in the above Tables I and II shows a distinct difference in amino acid composition between the ultimobranchial and the thyrocalcitonins (mamalian calcitonins). See M. Merle, G. Lefevre and G. Milhaud, Biochem. Biophy, Res. Comm., 87, (2) 455–460 (1979).

SUMMARY

Notwithstanding our failure to successfully purify crude ACTH or crude human calcitonin by applying the partition chromatography procedure using a selected solvent system, we have now discovered that we can apply partition chromatography using this same solvent system to crude salmon calcitonin or another ultimobranchial calcitonin to effectively purify these calcitonins.

When, in describing and claiming our invention, we make reference to particular types and kinds of calcitonins, such as human, pig, bovine, salmon, or eel calcitonin, it is understood that we mean to include the calcitonins of the same or similar structure whether obtained from natural or synthetic sources.

DISCLOSURE OF THE INVENTION

The selection of the crude hormone material to be purified and the preparation of the solvent mixture to be used in partition chromatography are critical factors in our invention.

The crude ultimobranchial calcitonin to be purified should preferably be obtained by solid phase synthesis such as is described in U.S. Pat. No. 3,915,949, using a resin as a support and in which the amino acids are assembled one-by-one with the resin support and protecting groups removed after the assemblage of the amino acid chain; this process of synthesis being known as the solid phase synthesis.

We may utilize equipment such as has heretofore been used in conducting partition chromatography except that we prefer to use a larger column than heretofore used in order to handle the larger volumes of crude material to be purified. A column 15 cm. in diameter and 120 cm in height has proved quite satisfactory.

The solvent mixture contains four principal ingredients which are designated (1) butanol (2) a lower aliphatic alcohol which may be ethanol, methanol or propanol or mixtures thereof (3) acetic acid or formic acid or mixtures thereof or ammonia (4) ammonium acetate or ammonium formate or mixtures thereof. We prefer to use acetic acid and ammonium acetate or formic acid and ammonium formate. As to the ammonium salt we prefer to use either 0.2 M ammonium acetate or 0.2 M ammonium formate.

Our process for the partitionaing of ultimobrancial calcitonin from crude mixtures thereof is effective when the solvent mixture has a pH within the range of 5.5 to 7.0. However, we prefer that the solvent mixture have a pH within the range of 6.0 to 6.8.

To adjust the solvent mixture to a desired pH within the ranges specified above, either acetic or formic acid may be added to the solvent mixture to lower the pH or ammonia may be added to raise the pH.

In the preparation of the solvent mixture to be used a mixture containing butanol, a lower aliphatic alcohol and an ammonium salt may, especially if ammonia is also contained, be more alkaline than is desired, and in this case the pH may be adjusted to the desired pH by the addition of acetic or formic acid. Or, the solvent mixture being prepared may be more toward the acid side than is desired and this may be adjusted to the addition to the mixture of dilute ammonia until the desired pH of the mixture is at the desired pH value. It is important, for the purification of ultimobranchial calcitonin that the pH of the solvent mixture which is utilized be within the range of 6.0 to 6.8 or at least within the range of 5.5 to 7.0. It is understood, of course, that any acid added to the mixture for the purpose of adjusting pH is regarded as being included within the solvent mixture utilized in the partition chromatography process, and likewise any ammonia added for the purpose of adjusting pH is regarded as being included in the solvent mixture of our partition chromatography process.

The column is packed, suitably with a fine dextran resin such as Sephadex. After being treated with acetic or formic acid, the Sephadex is introduced into the column in the form of a slurry. The solvent reservoir is supported at a height above the level of the column. The solvent mixture is stirred vigorously and allowed to stand for a time during which the two phases separate into an upper phase and a lower phase, these phases being separately collected.

The first essential step in the partition chromatography process is the equiliabration of the column to lower phase. The lower phase of the solvent system is added to the reservoir and caused to flow through the column from top to bottom to equilibrate the system to the lower phase.

The column is then equilibrated to upper phase in the same manner by causing the upper phase of the solvent mixture to be passed through the column. Excess upper phase is then removed.

A quantity of crude ultimobranchial calcitonin to be purified is suitably dissolved in upper phase solvent which is placed over the bed of resin, and the solution allowed to penetrate completely into the resin.

Elution is begun by passing the upper phase solvent, by gravity, through the column. Suitably, the fraction collector is set up with large collector tubes; for example, tubes of about 25 × 200 mm., and fractions of about 50-70 ml. are collected. The flow rate may be expected to decrease as the elution proceeds; and if the collection is by time per tube, an increasing amount of time per fraction may be allowed. The calcitonin peak of interest may be expected to be eluted within the first 10 liters, while all components require approximately 22 liters for their elution. A large number of tubes (200 or more) may be filled.

The location of the desired peptide among the different fractions may be by use of the Folin-Lowry method of peptide determination. This test is well known in the art. Suitably, about 40 microliters may be taken from every second or third fraction and treated with the Folin-Lowry reagents. The absorption of each tube may be read at 625 nm. and recorded. The results may then be plotted as tube number vs. absorption, and a selection of the tubes to be pooled may be made on the basis of the resulting pattern.

To isolate each fraction, it is necessary to remove the alcohol. This may be done by azeotropic distillation. The resulting clear aqueous solution is ready for freezing and lyophilization.

The following specific examples demonstrate the use of our improved process.

EXAMPLE 1

A mixture consisting of 28 L of n-butanol, 7 L of ethanol and 35 L of 0.2 M ammonium acetate solution containing 14 ml. of glacial acetic acid was prepared in a 200 L container. The mixture was well stirred several times, then allowed to separate into two phases. The pH of the lower phase was 6.70.

The lower phase of about 30 L was separated from the upper phase, then the entire amount was passed through a large partition chromatography column (15 × 120 cm.) which had been stored in 0.2 M acetic acid. The reservoir was then filled with upper phase solvent and this was added to the column while draining from the bottom of the column until the phase boundary between upper and lower phases had just entered the column. At this point the effluent was collected in a graduated cylinder.

After 6,700 ml. of upper base solvent had passed through the column, its exit from the bottom of the column was noted by its separation on top of the previously eluted lower phase. The stopcock at the bottom of the column was closed and the top of the column was opened. The column was then drained until the liquid remaining on top of the bed just entered the bed. The crude salmon calcitonin to be purified had been made by solid phase synthesis in accordance with the process set forth in U.S. Pat. No. 3,926,938. A solution of 15 gm. of this crude salmon calcitonin in 500 ml. of upper phase solvent was then carefully layered on top of the bed. It was allowed to run through the column into a graduated tube container until it was all on the bed, then washed onto the column with 200 ml. portions of upper phase solvent. After these had passed onto the column, 1,500 ml. of upper phase solvent was added to the top of the bed, the cover replaced and the upper phase in the reservoir allowed to pass through the column bed. After 4,500 ml. of effluent was collected, the exit line was transferred to a fraction collector and fractions were collected containing 70 ml. per tube. The flow rate was about 9 ml. per minute. 250 tubes were collected. Based on the results of the Folin-Lowry analysis, tubes 73 through 105 were combined to give 2,300 ml. of liquid This mixture was diluted with 3 L of filtered water and then concentrated on a rotary evaporator until 1,200 ml. of solution remained. This remaining liquid was shell frozen and lyophilized to yield 6.96 gm. of a white powder.

An identical run using 12 gm. of crude salmon calcitonin gave 5.75 gm. of product. The products from these two runs were combined to provide 12.71 gms. of material which was then dissolved in 225 ml. of 0.3 M acetic acid. The solution was added to a fine dextran resin bed in a column 10 cm. × 100 cm. which had previously been equilibrated with 0.03 M acetic acid. The column was then eluted with the same solution. The effluent was monitored through a UV spectrophotometer at 280 nm. That portion of the curve corresponding to salmon calcitonin was collected (1,000 ml.) and lyophilized to yield 10.6 gm. of product.

Thin layer chromatography on a cellulose F plate in the system n-butanol-pyridine-acetic acid-water (21:12:2:15) revealed one spot with an $R_f$ of 0.46. Further testing indicated the product was of high purity.

The partition column may be regenerated by elution with 30 L of 20% acetic acid followed by elution with 30 L of 0.2 M acetic acid.

EXAMPLE 2

A resin bed was prepared as in Example 1, but in a column of size 2.5 cm. × 85 cm. The column was eluted with 1 L of lower phase from the system 1,200 ml. of n-butanol, 300 ml. of ethanol, and 1,200 ml. of a 0.25 M ammonium acetate containing 0.6 ml. of acetic acid. 142 ml. of upper phase was eluted from the column before the presence of upper phase in the effluent was noted. A sample of 295 mg. of crude salmon calcitonin in 15 ml. of upper phase was placed on the column and eluted with upper phase solvent. The effluent was collected in a manner similar to Example 1 with the aid of a fraction collector. The Folin-Lowry analysis indicated that tubes 28 to 36 (7 ml. per tube) contained the desired product. The contents of the tubes were combined, diluted with filtered water and concentrated on a rotary evaporator, followed by lyophilization. The product was then desalted on a dextran resin column as in Example 1 to yield 126 mg. of purified salmon calcitonin. The thin layer chromatograph and elution characteristics were identical to the product obtained by Example 1.

EXAMPLE 3

The procedure as set forth in Example 1 may be repeated using the same solvent mixture but substituting crude eel calcitonin for the salmon calcitonin of Example 1. A purified eel calcitonin product may be expected to be obtained having biological activity which is at least as great as the salmon calcitonin obtained in Example 1.

EXAMPLE 4

A resin bed was prepared as in Example 1, but in a column of size 2.5 cm.×93 cm. The column was eluted with 1.2 liters of lower phase from the system 1,600 ml of n-butanol, 400 ml of ethanol, and 2000 ml of 0.2 M ammonium formate adjusted to pH 6.75 with dilute aqueous ammonia. 156 ml of lower phase was eluted from the column before the presence of upper phase in the effluent was noted. A sample of 316.2 mg of crude salmon calcitonin in 3 ml of upper phase was placed on the column and eluted with upper phase solvent. The effluent was collected in a manner similar to Example 1, with the aid of a fraction collector. The Folin-Lowry analysis indicated that tubes 31 to 39 (6.5 ml per tube) contained the desired product. The contents of the tubes were combined, diluted with DI water and concentrated on a rotary evaporator, followed by lyophilization. The product was then desalted on a dextran resin column as in Example 1 to yield 76.5 mg of purified salmon calcitonin. The thin layer chromatography and elution were identical to the product obtained by Example 1.

EXAMPLE 5

A resin bed was prepared as in Example 1, but in a column of size 2.5 cm×93 cm. The column was eluted with 1.2 liters of lower phase from the system 1,600 ml of n-butanol, 400 ml of ethanol and 2000 ml of 0.2 m ammonium formate. The entire mixture adjusted to pH 6.15 with dilute formic acid. 154 ml of lower phase was eluted from the column before the presence of upper phase in the effluent was noted. A sample of 316 mgs of crude salmon calcitonin in 3 ml of upper phase was placed on the column and eluted with upper phase solvent. The effluent was collected in a manner similar to Example 1, with the aid of fraction collector. The Folin-Lowry analysis indicated that tubes 56 to 79 (4.5 ml per tube) contained the desired product. The contents of the tubes were combined, diluted with DI water and concentrated on a rotary evaporator followed by lyophilization. The product was then desalted in a dextran resin column as in Example 1 to yield 85.4 mgs of purified salmon calcitonin. The thin layer chromatography and elution were identical to the product obtained by Example 1.

While in the foregoing detailed explanation we have described certain ways in which the improved process may be carried out, it is understood that many changes may be made and many modifications may be practiced, all within the spirit of the invention and the scope of the appended claims.

We claim:

1. In a process for purifying crude ultimobranchial calcitonin the step of subjecting said crude ultimobrancial calcitonin to partition chromatography using a solvent mixture containing (1)n-butanol (2) a lower aliphatic alcohol selected from the group consisting of ethanol, methanol, propanol and mixtures thereof. (3) acetic acid or formic acid or mixtures thereof, or ammonia and (4)ammonium acetate or ammonium formate or mixtures thereof, said solvent mixture having a pH of from 5.5 to 7.0.

2. A process as set forth in claim 1 in which said crude ultimobranchial calcitonin is crude salmon calcitonin.

3. A process as set forth in claim 1 in which said crude ultimobrancial calcitonin is crude eel calcitonin.

4. A process as set forth in claim 1 in which said lower aliphatic alcohol is ethanol.

5. A process as set forth in claim 1 in which said crude ultimobranchial calcitonin is prepared by solid phase synthesis.

6. A process as set forth in claim 1 in which said solvent mixture has a pH of from 6.0 to 6.8.

7. A process as set forth in claim 1 in which said ingredient No. (3) is ammonia.

8. A process as set forth in claim 1 in which said ingredient No. (3) is ammonia and the pH of said solvent mixture is within the range of 6.0 to 6.8.

9. A process as set forth in claim 7 in which the pH of said mixture is initially above 7.0 including the step of adding acetic or formic acid to the mixture to reduce the pH of said solvent mixture to a value within the pH range of 5.5 to 7.0 prior to the utilization of said mixture in the step of partition chromatography.

10. A process as set forth in claim 8 in which the pH of said mixture is initially above 6.8 including the step of adding acetic or formic acid to the mixture to reduce the pH of said solvent mixture to a value within the pH range of 6.0 to 6.8 prior to the utilization of said mixture in the step of partition chromatography.

11. A process as set forth in claim 1 in which said ingredient No. (3) is acetic acid or formic acid in which the pH of said mixture is initially below 5.5 including the step of adding ammonia to the mixture to increase the pH of the mixture to a value within the range of 5.5 to 7.0 prior to its utilization in the step of partition chromatography.

12. A process as set forth in claim 1 in which said ingredient No. (3) is acetic acid or formic acid in which the pH of said mixture is initially below 6.0 including the step of adding ammonia to the mixture to increase the pH of the mixture to a value within therange of 6.0 to 6.8 prior to its utilization in the step of partition chromatography.

* * * * *